United States Patent [19]

Imran

[11] Patent Number: 5,236,424
[45] Date of Patent: Aug. 17, 1993

[54] CATHETER WITH RETRACTABLE CANNULA FOR DELIVERING A PLURALITY OF CHEMICALS

[75] Inventor: Mir A. Imran, Palo Alto, Calif.

[73] Assignee: Cardiac Pathways Corporation, Sunnyvale, Calif.

[21] Appl. No.: 894,080

[22] Filed: Jun. 5, 1992

[51] Int. Cl.$^5$ .............................................. A61M 25/00
[52] U.S. Cl. .................................... 604/280; 604/264; 604/48; 604/93; 606/185
[58] Field of Search ........................... 604/95, 134–136, 604/157, 164, 280, 281, 22, 21, 48, 93; 606/167, 170, 171, 185; 128/656–658, 4

[56] References Cited

U.S. PATENT DOCUMENTS

| | | | |
|---|---|---|---|
| 3,326,207 | 6/1967 | Egan | 128/2.06 |
| 3,703,899 | 11/1972 | Calinog | 604/264 |
| 4,210,146 | 7/1980 | Banko | 606/171 |
| 4,522,212 | 6/1985 | Gelinas et al. | 128/642 |
| 4,649,924 | 3/1987 | Taccardi | 128/642 |
| 4,660,571 | 4/1987 | Hess et al. | 128/784 |
| 4,699,147 | 10/1987 | Chilson et al. | 128/642 |
| 4,940,064 | 7/1990 | Desai | 128/784 |
| 4,945,912 | 8/1990 | Langberg | 128/642 |
| 5,010,894 | 4/1991 | Edhag | 128/784 |
| 5,031,510 | 7/1991 | Krauter | 92/92 |
| 5,152,754 | 10/1992 | Plyley et al. | 604/164 |

FOREIGN PATENT DOCUMENTS 2163055 8/1985 United Kingdom .

*Primary Examiner*—C. Fred Rosenbaum
*Assistant Examiner*—C. Maglione
*Attorney, Agent, or Firm*—Flehr, Hohbach, Test, Albritton & Herbert

[57] ABSTRACT

Catheter with a retractable cannula for delivering a plurality of chemicals comprising a flexible elongate member having a centrally disposed lumen and a plurality of circumferentially spaced apart lumens including first and second fluid passage lumens Flexible elongate member has proximal and distal extremities. An actuator member is slidably mounted in the centrally disposed lumen. Springs are disposed within the centrally disposed lumen and engage the actuator member for moving the actuator member between extended and retracted positions. A tool having a distal extremity is carried by the actuator member and has a flow passage therein extending through the distal extremity of the tool. First and second fittings are secured to the proximal extremity of the flexible elongate member and having passages therein in communication with the first and second fluid passage lumens in the flexible elongate element. The distal extremity of the flexible elongate member is capable of supplying fluid from said first and second fluid passage lumens to the flow passage in the tool when the tool has been advanced to an extended position.

7 Claims, 1 Drawing Sheet

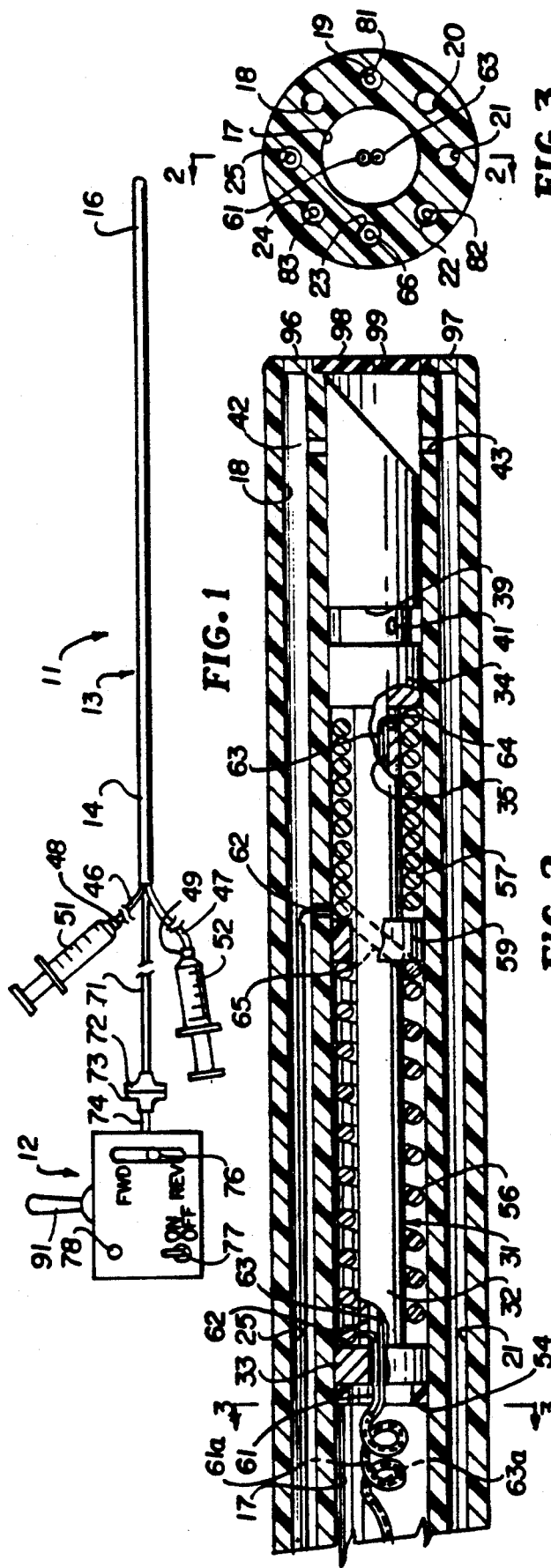

CATHETER WITH RETRACTABLE CANNULA FOR DELIVERING A PLURALITY OF CHEMICALS

BACKGROUND OF THE INVENTION

This invention relates to catheter with a retractable cannula for delivering a plurality of chemicals.

In the past, catheters have been provided for delivering a chemical to a site within the body of the patient. Typically, such catheters have been provided with a single lumen for delivering the chemical. If it is desired to deliver a second chemical to the same site, or even to a second site, the lumen in the catheter for delivering the first chemical must be flushed clear of the first chemical before the second chemical can be delivered. This has been found to be undesirable in many situations, particularly because it is difficult to control the amount of chemical which is delivered to the patient site. In addition, an undue amount of time is required for delivering the two chemicals to the site. There is therefore a need for a new and improved catheter which can be used for delivering a plurality of chemicals.

OBJECTS OF THE INVENTION

In general, it is an object of the present invention to provide a catheter with a retractable cannula for delivering a plurality of chemicals.

Another object of the invention is to provide a catheter of the above character in which it is unnecessary to flush one chemical from the catheter before the next chemical is delivered by the catheter.

Another object of the invention is to provide a catheter of the above character in which there is a minimum of mixing of the chemicals which are delivered.

Additional objects and features of the invention will appear from the following description in which the preferred embodiments are set forth in conjunction with the accompanying drawings.

BRIEF DESCRIPTION OF THE DRAWINGS

FIG. 1 is a side elevational view of a catheter with a retractable cannula for delivering a plurality of chemicals incorporating the present invention in conjunction with a control console utilized therewith.

FIG. 2 is an enlarged view partially in cross-section of the distal extremity of the catheter shown in FIG. 1 with the cannula being in a retracted position.

FIG. 3 is a cross-sectional view taken along the line 3—3 of

FIG. 4 is a cross-sectional view similar to that shown in FIG. 2 but showing the cannula in an extended position.

FIG. 5 is a cross-sectional view taken along the line 5—5 of FIG. 4.

DETAILED DESCRIPTION OF THE PREFERRED EMBODIMENT

In general, the catheter with a retractable cannula for delivering a plurality of chemicals is comprised of a flexible elongate member having a centrally disposed lumen and a plurality of circumferentially spaced apart lumens including first and second fluid passage lumens. The flexible elongate member has proximal and distal extremities. An actuator member is slidably mounted in the central lumen. Means is disposed within the central lumen and engaging the actuator member for moving the actuator member between extended and retracted positions. A tool having a distal extremity is carried by the actuator member and has a flow passage therein extending through the distal extremity. First and second fittings are secured to the proximal extremity of the flexible elongate member and are in communication with the first and second fluid passage lumens. Cooperative means is carried by the tool and the distal extremity of the flexible elongate member for supplying fluid from said first and second fluid passage lumens to the flow passage in the tool when the tool has been advanced to an extended position.

More particularly, the catheter with a retractable cannula for delivering a plurality of chemicals is shown in FIGS. 1 through 5 of the drawings and consists of a catheter 11 which is adapted to be connected to a control console 12. The catheter 11 consists of a flexible elongate member 13 formed of a suitable material such as plastic which is provided with proximal and distal extremities 14 and 16. The flexible elongate member is provided with a central lumen 17 and a plurality of circumferentially spaced apart lumens 18–25 which include at least first and second fluid passage lumens. Thus, as shown, lumens 21 and 25 are fluid passage lumens and are disposed diametrically of the flexible elongate member. An actuator member 31 is slidably mounted in the central lumen 17 at the distal extremity 16 of the flexible elongate member 13.

The actuator member 31 consists of a cylindrical or tubular rod 32 which has circular disks 33 and 34 mounted on the proximal and distal extremities of the rod 32. The tube 32 is provided with a bore 35 that extends axially thereof. The disk 34 is formed integral with a tool 36 which is the form of a circular cannula which is provided with an inclined cutting edge 37.

Cooperative means is carried by the tool and the distal extremity of the flexible elongate member 13 for supplying fluid from the first and second fluid passage lumens 21 and 25 to a flow passage 38 provided in the cannula or tool 36 and extending through the distal extremity of the same. This means includes an annular recess 39 in the tool 36 which has a plurality of circumferentially space apart, radially extending holes 41 extending from the annular recess 39 into the passage 38. The annular recess is adapted to be moved into registration with holes 42 and 43 provided in the flexible elongate member 13 and extending from the fluid passage lumens 21 and 25, respectively. Means is provided for supplying a fluid such as a liquid chemical to the fluid passage lumens 21 and 25, and consists of tubular members 46 and 47 which have flow passages therein in communication with the fluid passage lumens 21 and 25, respectively. Luertype fittings 48 and 49 are mounted on the proximal extremities of the tubular members 46 and 47 which are adapted to be connected to syringes 51 and 52 carrying the fluid, as for example the liquid chemicals that are to be used.

Means is provided within the central lumen 17 and engaging the actuator member 31 for moving the actuator member 31 between extended and retracted positions. The retracted position is determined by an annular stop 54 which is secured in the lumen 17 by suitable means such as an adhesive. Such means can be in the form of first and second helical springs 56 and 57 formed of a shape memory material such as Nitinol, which are coaxially disposed on the rod 32 with the proximal end of the spring 56 engaging the disk 33 and the distal extremity an annular member 59 provided within the central lumen 17 and secured to the wall forming the central lumen by suitable means such as an adhesive. The other or second helical spring 57 has its proximal extremity engaging the annular member 59 and his its distal extremity engaging the disk 34.

Means is provided for supplying electrical energy to the springs 56 and 57 and consists of a conductor 61 extending through the central lumen 17 and extending into the bore 35 and through a hole 62 in the tubular member 32 and connected to the proximal extremity of the spring 56 as shown in FIG. 2. Similarly, another conductor 63 extends through the central lumen 17 and the bore 35 and is connected to the distal extremity of the spring 57 through a hole 64 in the tubular member 32. The proximal extremity of the spring 57 is connected by a cross link 65 extending through a hole (not shown) in the annular member 59 to the distal extremity of the spring 56. The cross link 65 is connected to a common return conductor 66 through a hole 68. The common return conductor 66 extends through the lumen 21. The conductors 61 and 63 are provided with coil portions 61a and 63a to accommodate rectilinear movement of the actuator member 31.

The conductors 61 and 63 and the common return conductor 66 are connected at the proximal extremity of the flexible elongate member 14 into a cable 71 which is connected to a connector 72. The connector 72 is connected to a mating connector 73 which is connected by a cable 74 to the control console 12. The control console is provided with means for supplying energy to the cable 74 under the control of a slide mechanism 76 movable upwardly and downwardly for forward and reverse movement of the actuator member 31. The control console is the type disclosed in co-pending application Ser. No. 07/893,770, filed Jun. 5, 1992, (A-55929/HCH). The control console is provided with an on-off switch 77 and an indicator lamp 78 in the form of a light emitting diode to indicate when the power is turned on.

In order to make it possible to steer the distal extremity 16 of the catheter 11, means of the type disclosed in co-pending application Ser. No. 07/753,858, filed Nov. 18, 1991, is provided. As disclosed therein, such steering means can consist of first, second and third wires or elongate elements 81, 82 and 83 formed of a material having a negative coefficient of expansion such as Flexinol supplied by Toki of Japan. These elongate elements 81, 82 and 83 are disposed in the lumens 19, 22 and 24, and are offset approximately 120° with respect to each other. When more than three of such elongate elements are provided, they would be offset by angles of less than 120°. These elongate elements are connected to conductors which extend to the proximal extremity of the flexible elongate element through the lumens 19, 22 and 24, and are connected into the cable 71 and are connected to the control console 12. The distal extremities of the elongate elements 81, 82 and 83 are interconnected and are connected to the return conductor 66, which also extends into the cable 77 and is connected to the control console. The control console includes a joystick 91 which is pivotally movable through a cone extending through 360° and is used for selectively applying energy to the elements 81, 82 and 83 to cause bending or steering of the distal extremity of the catheter 11 in a manner described in co-pending application Ser. No. 07/793,858, filed Nov. 18, 1991.

A catheter constructed in accordance with the present invention can have a length ranging from 150 to 200 cm. It can have an outside diameter ranging from 0.030 inches to 0.120 inches. The cannula 36 can be in the form of a hypo tube which has been beveled to create the cutting edge 37. The hypo tube can have an outside diameter of a suitable size such as 0.015 inches.

Operation and use of the catheter with a retractable cannula for delivering a plurality of chemicals may now be briefly described as follows. Let is be assumed that a mapping and ablation procedure is underway with respect to the heart of a patient with the apparatus disclosed in co-pending application Ser. No. 07/656,764, filed Feb. 15, 1991. Let is be assumed that mapping has occurred and that it is desired to create a chemical ablation of a portion of the myocardium to destroy aberrant paths in the myocardium to eliminate arrhythmias in the heart of the patient. The catheter 11 of the present invention is inserted into the apparatus and is advanced into the appropriate chamber of the heart, as for example the left ventricle. This can be accomplished by the physician pushing on the proximal extremity of the catheter and causing the same to be advanced. In order to direct the distal extremity of the catheter appropriately, the surgeon can operate the joystick 91 to steer the distal extremity into the desired position as described in said co-pending application Ser. No. 07/793,858, filed Nov. 15, 1991.

The distal extremities of the fluid passage lumens 21 and 25 are closed by plugs 96 and 97 of a suitable plastic so that fluid cannot flow from those fluid passage lumens 21 and 25 through the distal extremity of the flexible elongate member 13. In order to prevent blood and other liquids from entering into the cannula 36 when it is in a retracted position and consists of a circular disk formed of a flexible material, as for example an elastomeric. The disk 98 is provided with a slit 99 through which the cannula 36 can extend.

After the distal extremity of the catheter 11 has been advanced so that it is in contact with the myocardium, the slider mechanism 76 can be operated to cause electrical energy to be supplied to the spring 57 to cause it to expand and to urge the cannula 36 distally through the slit 99 in the disk seal 98 to cause it to puncture the myocardium with the knife edge 37 of the cannula. As the cannula 36 is moved forwardly, the annular recess is moved into registration with the holes 42 and 43 which are in communication with the fluid passage lumens 21 and 25. As soon as this occurs, a desired chemical can be introduced by the use of syringe 51 into the tubular member 46 and into the fluid passage lumen 21 to cause it flow through the lumen 21 to the distal extremity of the catheter and then to pass through the hole 42 and thus into the annular recess 39 and through the holes 41 in the cannula and through the passage 78 provided in the cannula into the myocardium. This procedure is continued until the desired amount of chemical has been dispensed from the syringe 51.

Now let it be assumed that it is desired to dispense another chemical from the catheter. This can be readily accomplished by placing the chemical in the syringe 52 and operating the syringe the cause the chemical in the form of a liquid to be introduced through the tubular member 47 into the fluid passage lumen 25, and thence through the hole 43 into the annular recess 39 and through the holes 41 in the cannula 36 and through the passage 38, to again be disposed in the myocardium. It is easy to ascertain when registration has been achieved between the annular recess 39 and the holes 42 and 43 because this information will be communicated through the pressure column generated in the fluid passage lumens 21 and 25 as the liquid is being introduced into the lumens by syringes 51 and 52. If the annular recess was not in registration with the passages 42 and 43 it would not be possible to introduce the liquid through the catheter and this would be readily apparent from the physician operating the syringes 51 and 52.

Thus it can be seen that a plurality of chemicals and, in particular, two, as described herein, can be introduced into the myocardium without the necessity of flushing out the chemical which is provided in the other passage 21. Also it can be seen that there is very little intermixing of the two chemicals which have been introduced in the catheter itself. The common path travelled is basically the passage 38 provided in the cannula 36. As soon as the desired amounts and types of chemicals have been introduced into the myocardium, the cannula 36 can be retracted by operating the slider mechanism 76 to the reverse position to cause energization of the spring 56 to cause it to retract the actuator member 31. This is caused by the expansion of the spring 56. The catheter can then be withdrawn in a conventional manner.

From the foregoing it can be seen that a cannula has been provided which can be extended and retracted or moved forward and rearward without the necessity of pull wires and the like. This makes it possible to keep the distal extremity of the catheter relatively flexible while not making it unduly stiff by the use of pull wires.

In addition, it is possible to provide a catheter of the above character in which it is possible to deliver two different chemicals with a minimum amount of mixing between the two, and makes it possible to keep the chemicals separated until the approximately last one-quarter inch of the catheter, and also it is possible to deliver one chemical and then another without having to flush the catheter and without the necessity of mixing the two chemicals in the catheter over an extended length of the catheter.

It is easy to ascertain when registration has been achieved between the annular recess 39 and the holes 42 and 43 because this information will be communicated through the pressure column generated in the fluid passage lumens 21 and 25 as the liquid is being introduced into the lumens by the syringes 51 and 52. If the annular recess was not in registration with the passages 42 and 43 it would not be possible to introduce the liquid through the catheter and this would be readily apparent from the physician operating the syringes 51 and 52.

Thus it can be seen that there has been provided a catheter with a retractable cannula which makes it possible to deliver a plurality of chemicals to accomplish ablation or to deliver chemicals to tumor sites subcutaneously without the necessity of invading the tumor site with an external needle.

If it is desired to deliver more than two chemicals additional helical springs formed of a shape memory alloy can be provided on the actuator member 31 to provide additional positions for the actuator member 31 to move the cannula 36 into registration with another hole or holes (not shown) in communication with other fluid passage lumens (not shown) provided on the flexible elongate member 13.

What is claimed is:

1. A catheter with a retractable cannula for delivering a plurality of chemicals comprising, a flexible elongate member having a centrally disposed lumen and a plurality of circumferentially spaced apart lumens including first and second fluid passage lumens, said flexible elongate member having proximal and distal extremities, an actuator member slidably mounted in the centrally disposed lumen, means disposed with the centrally disposed lumen and engaging the actuator member for moving the actuator member between extended and retracted positions with respect to the flexible elongate member, a tool having a distal extremity carried by the actuator member and having a flow passage therein extending through the distal extremity of the took, first and second syringes secured to the proximal extremity of the flexible elongate member and having passages therein in communication with the first and second fluid passage lumens in the flexible elongate element, cooperative means carried by the tool on the distal extremity of the flexible elongate member for supplying fluid from said first and second fluid passage lumens to the flow passage in the tool when the tool has been advanced to an extended position.

2. A catheter as in claim 1 wherein said cooperative means includes an annular recess formed in the tool, holes formed in the annular recess extending into the flow passage in the tool, and holes in the distal extremity of the flexible elongate member in communication with the fluid flow passages and opening into the annular recess when the tool is in an extended position.

3. A catheter as in claim 1 wherein said tool is in the form of a cannula having a cutting edge.

4. A catheter as in claim 1 wherein said means for moving the actuator member further includes first and second helical springs having a negative coefficient of expansion and means for selectively energizing said first and second helical spring whereby when the first spring is energized, the actuator member is moved into an extended position, and when the second spring is actuated, the actuator member is moved to a retracted position.

5. A catheter as in claim 1 further including means for steering the distal extremity of the catheter.

6. A catheter as in claim 5 wherein said means for steering includes first, second and third elongate elements found with the circumferentially spaced apart lumens and spaced approximately 120° apart and means for selectively supplying energy to the first, second and third elongate elements to cause bending movement of the distal extremity of the catheter to thereby permit steering of the same.

7. A catheter as in claim 4 wherein said actuator member is in the form of a cylindrical rod having proximal and distal extremities and disks secured to the proximal and distal extremities and wherein the first and second springs are coaxially mounted on the rod between said disks together with an annular member disposed within the central lumen and secured to the distal extremity of the flexible elongate member, the distal extremity of the first helical spring engaging the annular member, the proximal extremity of the second spring also engaging the annular member.

* * * * *